United States Patent

Kanellakopulos et al.

[11] Patent Number: 5,814,645

[45] Date of Patent: Sep. 29, 1998

[54] ARYLOR HETARYL SUBSTITUTED NITROGEN HETEROCYCLES AND THEIR USE AS PESTICIDES

[75] Inventors: Johannes Kanellakopulos, Dormagen; Rainer Fuchs, Wuppertal; Johannes Rudolf Jansen, Monheim; Michael Schindler, Bergisch Gladbach; Christoph Erdelen, Leichlingen; Wolfgang Leicht, Leverkusen; Ulrike Wachendorff-Neumann, Bonn; Andreas Turberg, Erkrath, all of Germany

[73] Assignee: Bayer Aktiengesellschaft, Leverkusen, Germany

[21] Appl. No.: 916,719

[22] Filed: Aug. 18, 1997

Related U.S. Application Data

[63] Continuation of Ser. No. 522,351, Sep. 15, 1995.

[30] Foreign Application Priority Data

Mar. 24, 1993 [DE] Germany .......................... 43 09 552.6

[51] Int. Cl.$^6$ .......................... A61K 31/44; C07D 401/06
[52] U.S. Cl. .......................... 514/332; 514/335; 514/342; 546/262; 546/264; 546/266; 546/269.7
[58] Field of Search .................................. 546/262, 264, 546/266, 269.7; 514/332, 335, 342

[56] References Cited

U.S. PATENT DOCUMENTS

| 4,028,084 | 6/1977 | McNulty et al. ....................... 546/298 |
| 4,740,446 | 4/1988 | Schranz et al. ......................... 430/203 |
| 4,956,356 | 9/1990 | Diehr et al. ............................. 514/341 |

FOREIGN PATENT DOCUMENTS

| A-0272824 | 6/1988 | European Pat. Off. . |
| A-0357201 | 3/1990 | European Pat. Off. . |
| A-0367410 | 5/1990 | European Pat. Off. . |
| A-0402717 | 12/1990 | European Pat. Off. . |
| A-0500297 | 8/1992 | European Pat. Off. . |
| A-0530702 | 3/1993 | European Pat. Off. . |
| A-2637477 | 2/1978 | Germany . |
| WO-A-9005134 | 5/1990 | WIPO . |

OTHER PUBLICATIONS

Tetrahedron, (Incl. Tetrahedron Reports), vol. 35, Oxford GB, pp. 2591–2593, 1979.
Chemical Abstrascts, vol. 113, No. 1, (Jul. 2, 1990), Abstract No. 185r, V/G/Kulnevich et al., p. 179.
Abstract, vol. 24, No. 2, 1990, pp. 132–134.

*Primary Examiner*—Yogendra N. Gupta
*Attorney, Agent, or Firm*—Sprung Kramer Schaefer & Briscoe

[57] ABSTRACT

The present invention pertains to new substituted nitrogen heterocycles of general formula (I)

$$Q-\underset{R^2}{\underset{|}{\overset{R^1}{\underset{|}{C}}}}-N\overset{T}{\underset{X}{\diagdown}}Y_{\diagdown Z}$$
(I)

in which $R^1$ and $R^2$ independently of each other, stand for hydrogen or alkyl, X stands for oxygen, sulfur or an $NR^3$ group, Y stands for carbon (C or CH) or nitrogen, Z stands for an electron-attracting group, T stands for the remainder of an unsaturated ring system broken possibly by other heteroatoms or heteroatom groups, Q stands for possibly substituted aryl or possibly substituted hetaryl, wherein $R^3$ stands for hydrogen, alkyl or alkenyl, method for preparing them and their use as pesticides.

9 Claims, No Drawings

ARYLOR HETARYL SUBSTITUTED NITROGEN HETEROCYCLES AND THEIR USE AS PESTICIDES

This application is a continuation of application Ser. No. 08/522,351, filed on Sep. 15, 1995.

The present invention relates to new substituted nitrogen heterocycles, to a process for their preparation, and to their use as pesticides.

Substituted nitrogen heterocycles and their use as insecticides are disclosed in, for example, EP-OS European Offenlegungsschrift) 259,738. However, the activity of the known compounds is not always satisfactory.

New substituted nitrogen heterocycles of the general formula (I)

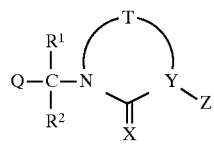

in which $R^1$ and $R^2$ independently of one another represent hydrogen or alkyl, X represents oxygen, sulphur or a radical $NR^3$, Y represents carbon (C or CM) or nitrogen, Z represents an electron-attracting group, T represents the radical of an unsaturated ring system which is optionally interrupted by further hetero atoms or groups of hetero atoms, Q represents optionally substituted aryl or optionally substituted hetaryl, in which $R^3$ represents hydrogen, alkyl or alkenyl, have been found.

Furthermore, it has been found that the new substituted nitrogen heterocycles of the general formula (I)

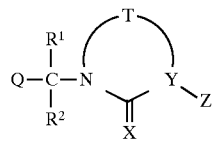

in which $R^1$ and $R^2$ independently of one another represent hydrogen or alkyl, X represents oxygen, sulphur or a radical $NR^3$, Y represents carbon (C or CH) or nitrogen, Z represents an electron-attracting group, T represents the radical of an unsaturated ring system which is optionally interrupted by further hetero atoms or groups of hetero atoms, Q represents optionally substituted aryl or optionally substituted hetaryl, in which $R^3$ represents hydrogen, alkyl or alkenyl, are obtained when nitrogen heterocycles of the formula (II)

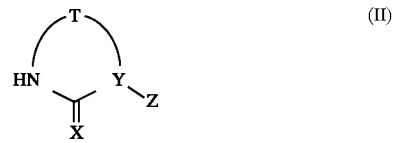

in which

T, Y and Z have the abovementioned meaning, are reacted with halogenomethyl compounds of the formula (III)

in which

Hal represents chlorine, bromine or iodine and Q, $R^1$ and $R^2$ have the abovementioned meaning, if appropriate in the presence of a diluent and in the presence of a base.

Formula (I) also embraces the tautomeric forms of the compounds according to the invention, for example

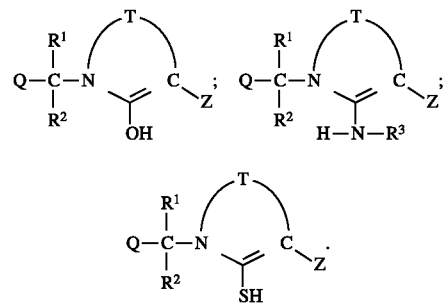

Alkyl in the general formulae denotes straight-chain or branched alkyl having advantageously 1 to 20, particularly advantageously 1 to 18 and very particularly advantageously 1 to 16, carbon atoms. Alkyl preferably contains 1 to 8, particularly preferably 1 to 6 and very particularly preferably 1 to 4, carbon atoms, specific mention being made of methyl, ethyl, n- and i-propyl and n-, i-, s- and t-butyl.

Alkenyl in the general formulae denotes straight-chain or branched alkenyl having preferably 1 double bond and preferably 2 to 8, in particular 3 to 6 and very particularly preferably 3 or 4, carbon atoms, specific mention being made of the allyl group.

Aryl in the general formulae preferably denotes naphthyl and phenyl, particularly preferably phenyl.

Aralkyl in the general formulae preferably denotes naphthylalkyl or phenylalkyl, particularly preferably phenylalkyl. The alkyl moiety is straight-chain or branched and contains preferably 1 to 6, particularly preferably 1 to 4 and very particularly preferably 1 or 2, carbon atoms. Specific mention may be made of benzyl and phenylethyl.

Hetaryl in the general formulae denotes heteroaromatic 5- to 7-membered rings having preferably 1 to 3, in particular 1 or 2, identical or different hetero atoms. Preferred hetero atoms are oxygen, sulphur or nitrogen. The following may be mentioned by way of example and as being preferred: pyrryl, furyl, thienyl, thiazolyl, pyridyl, pyrazolyl and pyrimidinyl.

The optionally substituted radicals which are listed in the general formulae can have one or more, preferably 1 to 3, in particular 1 or 2, identical or different substituents. The following substituents may be listed by way of example and as being preferred: alkyl having preferably 1 to 8, in particular 1 to 6 and very particularly preferably 1 to 4, carbon atoms, such as methyl, ethyl, n- and i-propyl and n-, i- and t-butyl; alkoxy having preferably 1 to 8, in particular 1 to 6 and very particularly preferably 1 to 4, carbon atoms, such as methoxy, ethoxy, n- and i-propyloxy and n-, i- and t-butyloxy; alkylthio having preferably 1 to 8, in particular 1 to 6 and very particularly preferably 1 to 4, carbon atoms, such as methylthio, ethylthio, n- and i-propylthio and n-, i- and t-butylthio; halogenoalkyl and halogenoalkoxy having preferably 1 to 8, in particular 1 to 6 and very particularly preferably 1 to 4, carbon atoms and preferably 1 to 7, in particular 1 to 5 and very particularly preferably 1 to 3, halogen atoms, the halogen atoms being identical or different and preferably being fluorine, chlorine or bromine, in particular fluorine, such as trifluoromethyl or trifluoromethoxy; hydroxyl; amino; halogen, preferably fluorine, chlorine, bromine and iodine, in particular fluorine, chlorine and bromine; cyano, nitro, phenyl which is optionally substituted by the abovementioned radicals; alkylcarbonyloxy having preferably 1 to 6, in particular 1 to 4 and very particularly preferably 1 or 2, carbon atoms in the alkyl group, or a heteroaliphatic or heteroaromatic radical, such as pyridyl, furyl or tetrahydrofuryl.

Furthermore, it has been found that the new substituted nitrogen heterocycles of the formula (1) are distinguished by outstanding insecticidal activity.

Preferred substituted nitrogen heterocycles of the formula (I) are those in which $R^1$ represents hydrogen or $C_{1-4}$-alkyl, $R^2$ represents hydrogen, X represents oxygen, sulphur or a radical $NR^3$, Y represents carbon (C or CH) or nitrogen, Z represents a cyano or a nitro group or optionally substituted alkylsulphonyl, trifluoroacetyl or trifluoroalkyl radicals, T represents the radical of a five-, six- or seven-membered unsaturated ring system which is optionally interrupted by further hetero atoms or groups of hetero atoms, Q represents aryl or hetaryl, each of which is optionally monosubstituted or polysubstituted by halogen, $C_{1-6}$-alkyl, $C_{1-6}$-alkoxy, $C_{1-6}$halogenoalkyl, $C_{1-6}$-halogenoalkoxy, nitro or cyano, in which $R^3$ represents hydrogen, $C_{1-6}$alkyl or $C_{3-8}$-alkenyl.

Particularly preferred compounds of the formula (I) are those in which the group

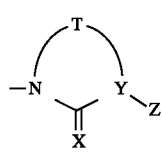

assumes one of the following meanings 1 to 25:

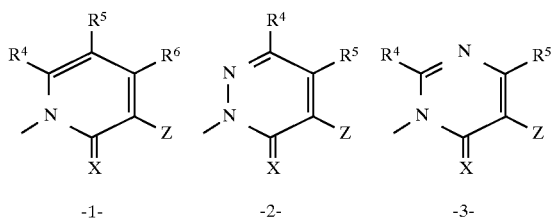

-1-  -2-  -3-

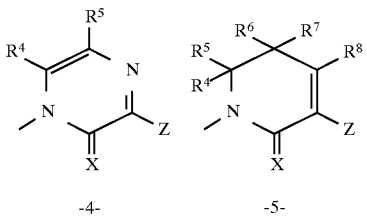

-4-  -5-

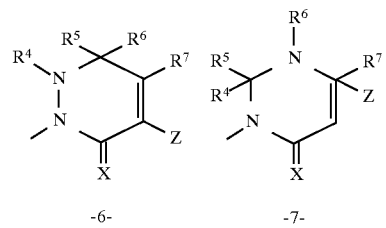

-6-  -7-

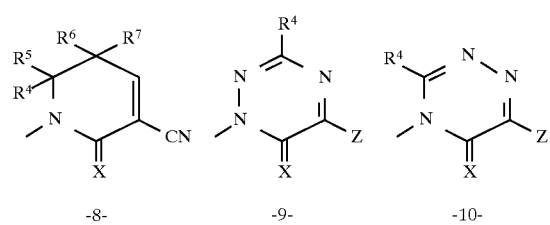

-8-  -9-  -10-

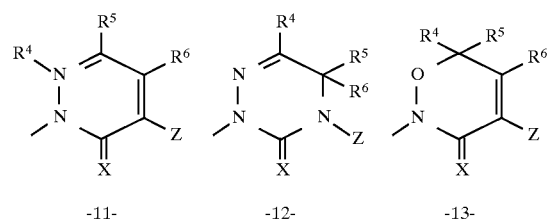

-11-  -12-  -13-

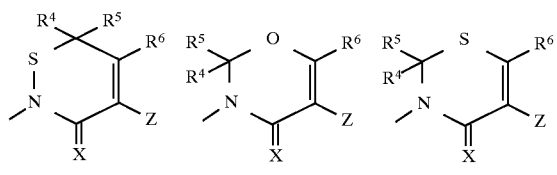

-14-  -15-  -16-

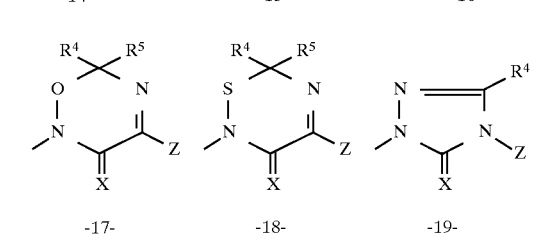

-17-  -18-  -19-

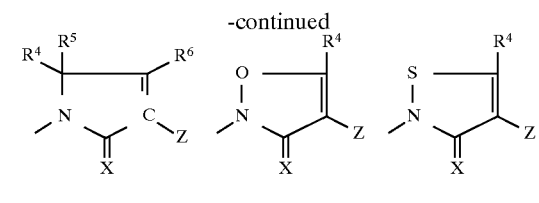
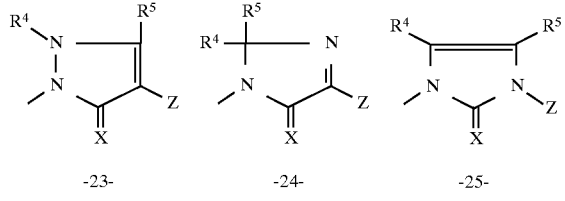

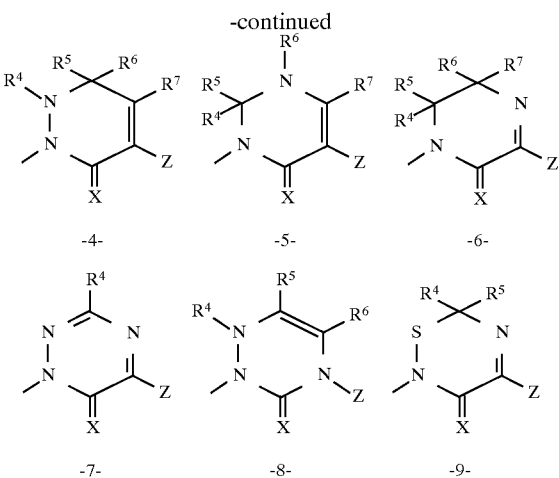

where, in the formulae 1 to 25, $R^1$ represents hydrogen or $C_{1-3}$-alkyl, $R^2$ represents hydrogen, X represents oxygen, sulphur or a radical $NR^3$, Z represents a cyano, nitro, trifluoroacetyl or trifluoromethyl group, Q represents aryl or five- or six-membered hetaryl, each of which is optionally mono- or polysubstituted by halogen, $C_{1-4}$-alkyl, $C_{1-4}$-alkoxy, $C_{1-4}$-halogenoalkoxy, $C_{1-4}$-halogenalkyl, nitro or cyano, $R^3$ represents hydrogen, $C_{1-4}$-alkyl or $C_{3-6}$-alkylene, and $R^4$, $R^5$, $R^6$, $R^7$, and $R^8$ independently of one another represent hydrogen, halogen, $C_{1-4}$alkyl, which is optionally substituted by halogen, or $C_{1-4}$-alkoxy, phenyl which is optionally substituted by halogen, $C_{1-5}$-alkyl, $C_{1-5}$-alkoxy, $C_{1-5}$-halogenoalkyl or $C_{1-5}$-halogenoalkoxy, or benzyl which is optionally substituted by halogen, $C_{1-5}$-alkyl, $C_{1-5}$-halogenoalkyl or $C_{1-5}$-alkoxy.

Very particularly preferred compounds of the formula (I) are those in which the group

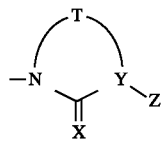

assumes one of the following meanings 1 to 14:

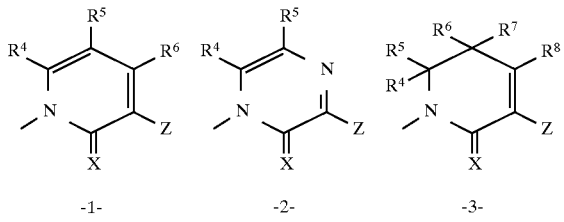

where $R^1$ represents hydrogen, methyl or ethyl, $R^2$ represents hydrogen,

X represents oxygen, sulphur or $NR^3$,

Z represents a cyano or nitro group,

Q assumes one of the following meanings 1 to 4:

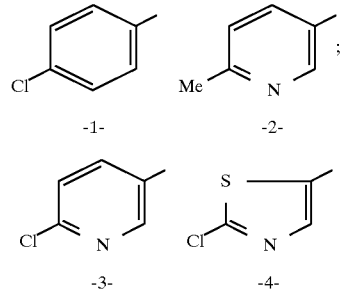

$R^3$ represents hydrogen or methyl, and $R^4$, $R^5$, $R^6$, $R^7$ and $R^8$ independently of one another represent hydrogen, fluorine, chlorine, bromine, $C_{1-2}$-alkyl, $C_{1-2}$-alkoxy and phenyl which is optionally mono- or polysubstituted by fluorine, chlorine, bromine, $C_{1-2}$-alkyl, trifluoromethyl, $C_{1-2}$-alkoxy or trifluoromethoxy.

If, according to the process, 3-cyano-2-hydroxypyridine and 4-chlorobenzyl chloride are used as starting materials, the course of the process according to the invention can be represented by the following equation:

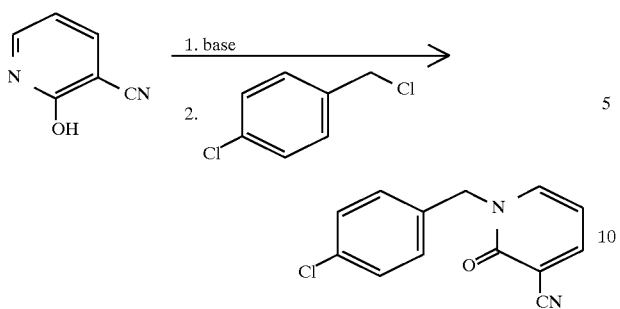

The compounds of the formula (II)

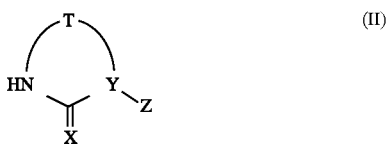

in which

T, X, Y and Z have the abovementioned meanings,
which are required as starting material in the above process, are known or can be prepared by processes known in principle. For example, 3-cyano-pyridones of the formula (II-1) are obtained when 1,3-diketones of the formula (IV)

in which $R^9$ and $R^{11}$ independently of one another represent hydrogen or $C_{1-3}$-alkyl, and $R^{10}$ represents hydrogen or $C_{1-3}$-alkyl or halogen, are subjected to a condensation reaction with cyanoacetamide (J. Heterocycl. Chem. 19, 1297–1300 (1982)).

The compounds of the formula (III)

in which

Hal, $R^1$, $R^2$ and Q have the abovementioned meanings, which are required as starting material in the above process, are known or can be obtained by processes known in principle (JP 48 099 178; DE 4,016,175; DE 3,631,538).

The process is characterized in that compounds of the formula (II) in which T, X, Y and Z have the abovementioned meanings, are reacted with compounds of the formula (III) in which Hal, $R^1$, $R^2$ and Q have the abovementioned meanings, in the presence of acid acceptors.

Acid acceptors which can be employed in the process according to the invention are all acid-binding agents which can conventionally be used for reactions of this type. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate, sodium hydrogen carbonate, potassium carbonate, potassium hydrogen carbonate and calcium carbonate, alkali metal acetates, such as sodium acetate and potassium acetate, alkali metal alcoholates, such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4,3,0]-non-5-ene (DBN), 1,8-diazabicyclo[5,4,0]-undec-7-ene (DBU) and 1,4diazabicyclo-[2,2,2]-octane (DABCO).

The process according to the invention for the preparation of the new compounds of the formula (I) is preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethyl sulphoxide, tetramethylene sulphone and hexamethylphosphoric triamide.

When carrying out the process according to the invention, the reaction temperatures can be varied within a substantial range. In general, the process is carried out at temperatures between 0° C. and 200° C., preferably at temperatures between 20° C. and 150° C.

The process according to the invention is generally carried out under atmospheric pressure. However, it is also possible to carry out the process under increased or reduced pressure.

To carry out the process according to the invention, the starting substances required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the temperature required in each case. Working-up in the process according to the invention is carried out in each case by customary methods (compare the preparation examples).

The active compounds are suitable for combating animal pests, preferably arthropods and nematodes, in particular insects and arachnids, which are encountered in agriculture, in forests, in the protection of stored products and of materials, and in the hygiene sector. They are active against normally sensitive and resistant species and against all or individual development stages. The abovementioned pests include:

From the order of the Isopoda, for example, *Oniscus asellus, Armadillidium vulgare* and *Porcellio scaber.*

From the order of the Diplopoda, for example, *Blaniulus gutulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus* corporis, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides, Tribolium spp., Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, Acarus siro, Argas spp., Omithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The active compounds according to the invention are not only active against plant, hygiene and stored product pests, but also, in the veterinary medicine sector, against animal parasites (ectoparasites and endoparasites), such as scaly tics, Argasidae, scab mites, Trombidae, flies (stinging and sucking), parasitic fly larvae, lice, hair lice, bird lice, fleas and endoparasitic worms.

They are active against normally sensitive and resistant species and strains and against all parasitic and non-parasitic stages of development of the ecto- and endoparasites.

The active compounds according to the invention are distinguished by powerful insecticidal and acaricidal activity.

The active compounds can be converted into the customary formulations, such as solutions, emulsions, wettable powders, suspensions, powders, dusts, pastes, soluble powders, granules, suspension/emulsion concentrates, natural and synthetic substances impregnated with active compound, and very fine capsules in polymeric substances.

These formulations are produced in a known manner, for example by mixing the active compounds with extenders, that is, liquid solvents and/or solid carriers, optionally with the use of surface-active agents, that is, emulsifing agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuff, and trace nutrients such as salts of iron, manganese, boron, copper, cobalt, molybdenum and zinc.

The formulations in general contain between 0.1 and 95 per cent by weight of active compound, preferably between 0.5 and 90%.

Mixtures with other known active compounds, such as fungicides, insecticides, acaricides, nematicides, bird repellants, plant nutrients and agents which improve the soil structure, are also possible.

The good toleration of the active compounds by plants, at the concentrations required for combating pests, permits treatment of above-ground parts of plants, of vegetable propagation stock and seed, and of the soil.

The active compounds can be used as such or in the form of their formulations or the use forms prepared therefrom by further dilution, such as ready-to-use solutions, suspensions, emulsions, powders, pastes and granules. They are used in the customary manner, for example by watering, spraying, atomizing, scattering and by treating the seeds.

The active compounds according to the invention can be applied before or after emergence of the plants.

They can also be applied by pre-plant-incorporation.

The amount of active compound applied can be varied within a substantial range. It depends essentially on the nature of the desired effect. In general, the application rates are between 0.01 and 10 kg of active compound per hectare of soil surface, preferably between 0.05 and 5 kg per ha.

EXAMPLE A

Phaedon larvae test

Solvent: 7 parts by weight of dimethyl formamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the plants are populated with mustard beetle (*Phaedon cochleariae*) larvae. After 3 days, the destruction in % is determined. 100% means that all the beetle larvae have been killed; 0% means that none of the beetle larvae have been killed.

In this test, superior activity compared with the prior art is shown, for example for the following compounds of the preparation examples: 1 and 2.

TABLE (Plant-damaging insects)
Phaedon larvae test

| Active compounds | Active compound concentration in % | Degree of destruction in % after 7 days |
|---|---|---|
| [structure: 6-chloro-pyridin-3-ylmethyl linked to 3-cyano-pyridin-2(1H)-one] | 0.1 | 100 |
| [structure: 2-chloro-thiazol-5-ylmethyl linked to 3-cyano-pyridin-2(1H)-one] | 0.1 | 100 |

EXAMPLE B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, superior activity compared with the prior art is shown, for example for the following compounds of the preparation examples: 1 and 2.

TABLE (Plant-damaging insects)
Plutella test

| Active compounds | Active compound concentration in % | Degree of destruction in % after 7 days |
|---|---|---|
| 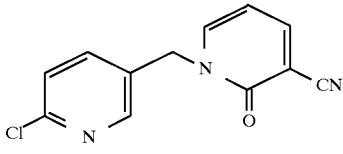 | 0.1 | 100 |
| 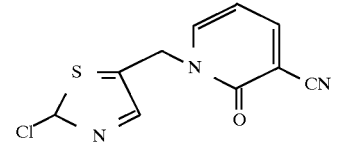 | 0.1 | 100 |

EXAMPLE C

Nephotettix test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice leaf hopper (*Nephotettix cincticeps*) while the seedlings are still moist.

After the specified period of time, the destruction in % is determined. 100% means that all the leaf hoppers have been killed; 0% means that none of the leaf hoppers have been killed.

In this test, superior activity compared with the prior art is shown, for example for the following compounds of the preparation examples: 1 and 2.

EXAMPLE D

Myzus test

Solvent: 31 parts by weight of acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-water to the desired concentration.

Field bean (*Vicia faba*) seedlings which are infested with the green peach aphid (*Myzus persicae*) are dipped into the preparation of active compound at the desired concentration and placed into a plastic container.

After the specified period of time, the destruction in % is determined. 100% means that all animals have been killed; 0% means that none of the animals have been killed.

In this test, the superior activity compared with the prior art is shown, for example, by the following compound of the preparation examples: 1.

TABLE (Plant-damaging insects)
Nephotettix test

| Active compounds | Active compound concentration in % | Degree of destruction in % after 6 days |
|---|---|---|
| 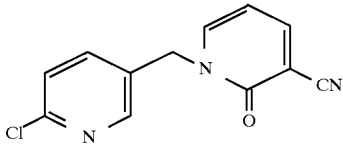 | 0.1 | 100 |
| 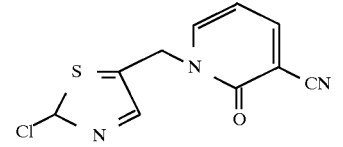 | 0.1 | 100 |

TABLE

(Plant-damaging insects)
Myzus test

| Active compounds | Active compound concentration in % | Degree of destruction in % after 2 days |
|---|---|---|
| 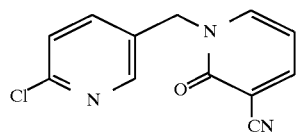 | 0.1<br>0.01<br>0.001 | 100<br>100<br>99 |

Preparation Examples

Example 1

2.0 g (0.017 mol) of 3-cyano-2-pyridone (Braña, Rodriguez, J. Heterocycl. Chem., 1297 (1982)) are dissolved in 30 ml of absolute N,N-dimethylformamide, and 0.56 g (0.019 mol) of sodium hydride (80% suspension) are added at 0° C. After the mixture has been stirred for 20 minutes, a solution of 2.75 g (0.017 mol) of 2-chloro-5-chloromethyl pyridine in 10 ml of absolute acetonitrile is added dropwise, and the mixture is stirred for 3 hours at room temperature. The reaction mixture is then poured into 400 ml of water and extracted using ethyl acetate, and the organic phase is dried over magnesium sulphate and then distilled to dryness. The residue is stirred with a little diethyl ether and filtered off with suction. In this manner, 3.2 g of 1-(2'-chloropyridin-3-yl)-3-cyano-2-pyridone of melting point 145° C. are obtained.

The following were obtained analogously:

TABLE 1

| Example No | Q | X | R¹ | R² | Physical data mp. |
|---|---|---|---|---|---|
| 2 | (5-chloro-thiazol-2-yl)methyl | 3-cyano-2-pyridon-1-yl | H | H | 148° C. |
| 3 | (4-chlorophenyl)methyl | 3-cyano-2-pyridon-1-yl | H | H | 142° C. |
| 4 | (6-chloropyridin-3-yl)methyl | 3-nitro-2-pyridon-1-yl | H | H | 154° C. |
| 5 | (6-chloropyridin-3-yl)methyl | 4-ethoxy-3-cyano-2-pyridon-1-yl | H | H | 162–163° C. |

TABLE 1-continued
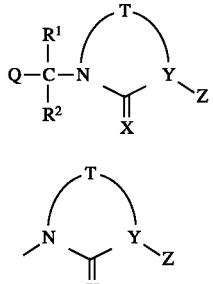
| Example No | Q | X | R¹ | R² | Physical data mp. |
|---|---|---|---|---|---|
| 6 | 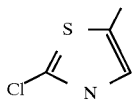 | 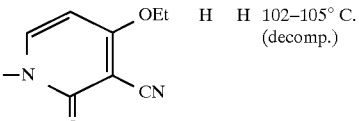 | H | H | 102–105° C. (decomp.) |
| 7 | 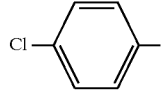 | 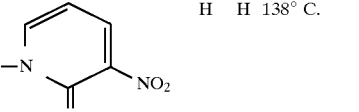 | H | H | 138° C. |
| 8 | 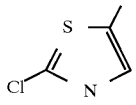 | 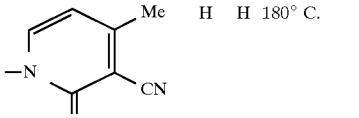 | H | H | 180° C. |
| 9 | 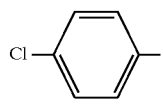 | 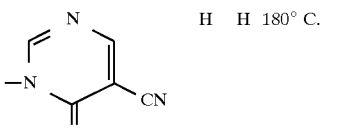 | H | H | 180° C. |
| 10 | 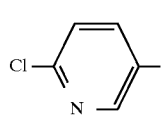 | 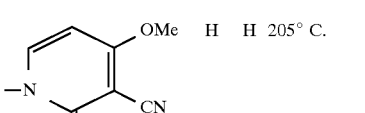 | H | H | 205° C. |
| 11 | 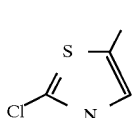 | 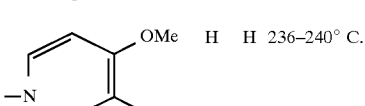 | H | H | 236–240° C. |
| 12 | 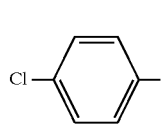 | 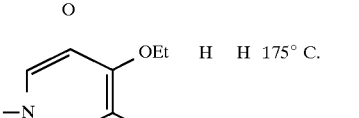 | H | H | 175° C. |
| 13 | 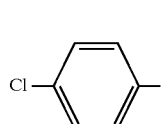 | 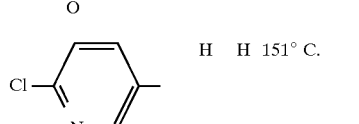 | H | H | 151° C. |
| 14 | 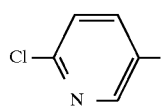 | 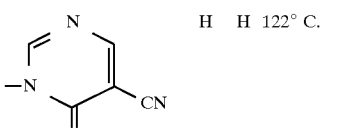 | H | H | 122° C. |

TABLE 1-continued

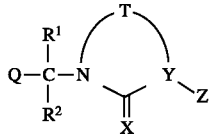

| Example No | Q | [structure with T, N, Y, Z, X] | R¹ | R² | Physical data mp. |
|---|---|---|---|---|---|
| 15 | [6-chloropyridin-3-yl] | [N-CH₂-CH₂-N(CN)-C(=O) ring] | H | H | D₆ DMSO δ=8.37(d, 1H); 7.80 (dd, 1H); 7.53(d, 1H); 4.41(s, 2H) |
| 16 | [2-chlorothiazol-5-yl] | [N-CH₂-CH₂-N(CN)-C(=O) ring] | H | H | CDCl₃ δ=7.47(s, 1H); 4.57 (s, 2H); 3.92(m, 2H; 3, 52 (m, 3H) |
| 17 | [6-chloropyridin-3-yl] | [N-CH₂-CH₂-CH₂-N(CN)-C(=O) ring] | H | H | DMSO δ=8.36(d, 1H; 7.79(dd, 1H); 7.52(d, 1H); 4.52 (s, 2H) |
| 18 | [2-chlorothiazol-5-yl] | [N-CH₂-CH₂-CH₂-N(CN)-C(=O) ring] | H | H | CDCl₃ δ=7.46(s, 1H); 4.63 (s, 2H); 3.80(t, 2H); 3.39 (t, 2H) |
| 19 | [3,4-dichlorophenyl] | [3-cyano-2-oxopyridin-1-yl] | H | H | 138° C. |
| 20 | [2,4,5-trichlorophenyl] | [3-cyano-2-oxopyridin-1-yl] | H | H | 136° C. |
| 21 | [2,3-dichlorophenyl with Cl] | [3-cyano-2-oxopyridin-1-yl] | H | H | 176° C. |
| 22 | [6-chloropyridin-3-yl] | [5-methyl-3-cyano-2-oxopyridin-1-yl] | H | H | 143° C. |
| 23 | [4-fluorophenyl] | [3-cyano-2-oxopyridin-1-yl] | H | H | 97–99° C. |

TABLE 1-continued

| Example No | Q | X (group) | R¹ | R² | Physical data mp. |
|---|---|---|---|---|---|
| 24 | 4-Cl-3-F-phenyl | 3-cyano-2-oxo-pyridin-1-yl | H | H | 160° C. |
| 25 | 6-chloro-pyridin-3-yl | 5-benzyl-3-cyano-2-oxo-pyridin-1-yl (CH₂-phenyl substituent) | H | H | DMSO δ=8.45(d, 1H); 8.30 (d, 1H); 8.12(d, 1H); 7.81 (m, 1H); 7.53(d, 1H); |
| 26 | 3,4-difluoro-phenyl | 3-cyano-2-oxo-pyridin-1-yl | H | H | 125–128° C. |
| 27 | 4-chloro-phenyl | 3-cyano-6-methyl-2-oxo-pyridin-1-yl | H | H | 158° C. |
| 28 | 4-chloro-phenyl | 5-chloro-3-cyano-4,6-dimethyl-2-oxo-pyridin-1-yl | H | H | 129° C. |
| 29 | 4-chloro-phenyl | 5-bromo-3-cyano-4,6-dimethyl-2-oxo-pyridin-1-yl | H | H | 152° C. |
| 30 | 4-chloro-phenyl | 3-cyano-4-methyl-2-oxo-pyridin-1-yl | H | H | 118° C. |
| 31 | 2-chloro-thiazol-5-yl | 3-nitro-2-oxo-pyridin-1-yl | H | H | 148° C. |

TABLE 1-continued
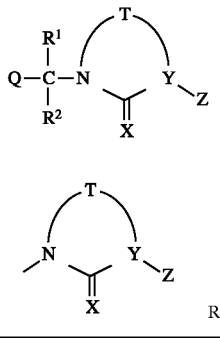
| Example No | Q | X | R¹ | R² | Physical data mp. |
|---|---|---|---|---|---|
| 32 | 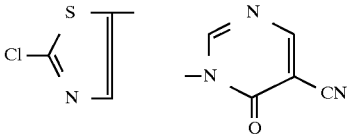 | 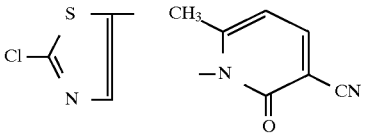 | H | H | 116–121° C. |
| 33 | 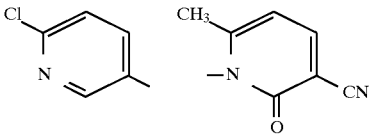 | 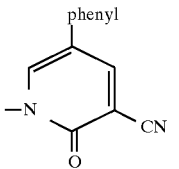 | H | H | 148° C. |
| 34 | 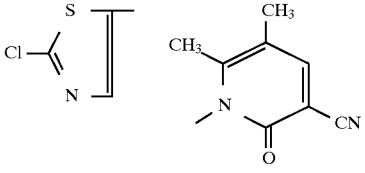 | 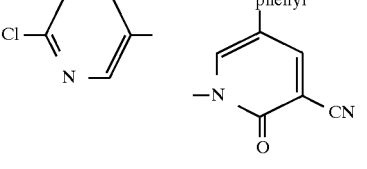 | H | H | 172° C. |
| 35 | 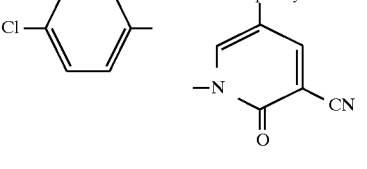 | 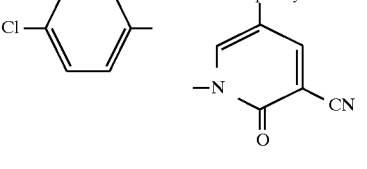 | H | H | 183° C. |
| 36 | | | H | H | 188° C. |
| 37 | | | H | H | 145° C. |
| 38 | | | H | H | 155° C. |

TABLE 1-continued

| Example No | Q | [structure] | R¹ | R² | Physical data mp. |
|---|---|---|---|---|---|
| 39 | 4-Cl-phenyl | 5,6-dimethyl-1-methyl-3-CN-pyridin-2-one | H | H | 102° C. |
| 40 | 6-Cl-pyridin-3-yl | 6-methyl-4-CF₃-3-CN-pyridin-2-one | H | H | 145° C. |
| 41 | 2-Cl-thiazol-5-yl | 6-methyl-4-CF₃-3-CN-pyridin-2-one | H | H | 67–69° C. |
| 42 | 4-Cl-phenyl | 6-methyl-4-CF₃-3-CN-pyridin-2-one | H | H | 125° C. |
| 43 | 2-Cl-thiazol-5-yl | 5-Cl-6-methyl-4-methyl-3-CN-pyridin-2-one | H | H | 115° C. |
| 44 | 4-F-phenyl | 3-CN-pyridin-2-one | H | H | 135° C. |

We claim:

1. Substituted nitrogen heterocycles of the formula (I)

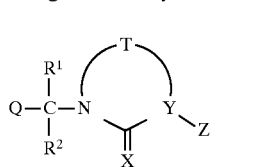

(I)

in which the group

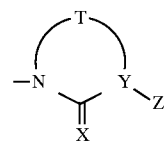

represents one of the following meanings:

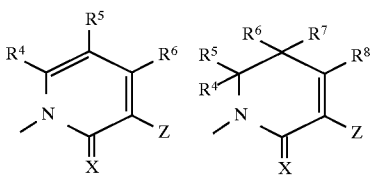

where

R$^1$ represents hydrogen, methyl or ethyl,
R$^2$ represents hydrogen,
X represents oxygen, sulphur or NR$^3$,
Z represents a cyano or nitro group,
Q assumes one of the following meanings

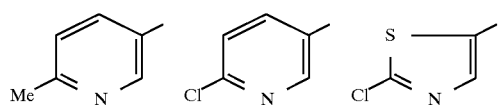

R$^3$ represents hydrogen or methyl, and
R$^4$, R$^5$, R$^6$, R$^7$ and R$^8$ independently of one another represent hydrogen, fluorine, chlorine, bromine, C$_{1-2}$-alkyl, C$_{1-2}$-alkoxy and phenyl which is optionally mono- or polysubstituted by fluorine, chlorine, bromine, C$_{1-2}$-alkyl, trifluoromethyl, C$_{1-2}$-alkoxy or trifluoromethoxy.

2. Process for the preparation of substituted nitrogen heterocycles of the formula (I)

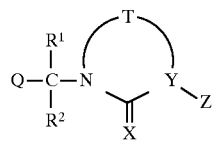

in which the group

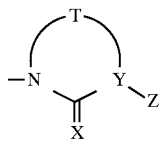

represents one of the following meanings:

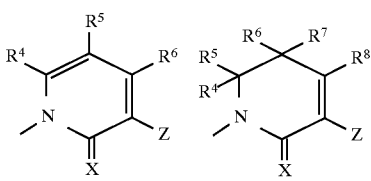

where

R$^1$ represents hydrogen, methyl or ethyl,
R$^2$ represents hydrogen,
X represents oxygen, sulphur or NR$^3$,
Z represents a cyano or nitro group, Q assumes one of the following meanings

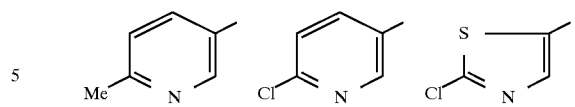

R$^3$ represents hydrogen or methyl, and
R$^4$, R$^5$, R$^6$, R$^7$ and R$^8$ independently of one another represent hydrogen, fluorine, chlorine, bromine, C$_{1-2}$-alkyl, C$_{1-2}$-alkoxy and phenyl which is optionally mono- or polysubstituted by fluorine, chlorine, bromine, C$_{1-2}$-alkyl, trifluoromethyl, C$_{1-2}$-alkoxy or trifluoromethoxy, wherein nitrogen heterocycles of the formula (II)

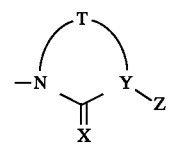

in which the group

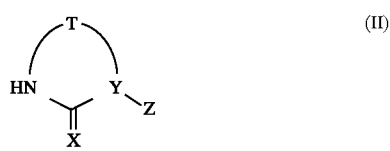

is as defined hereinbefore are reacted with halogeno-methyl compounds of the formula (III)

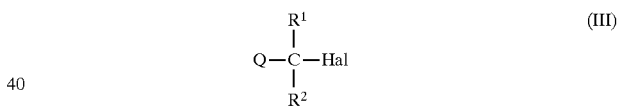

in which

Hal represents chlorine, bromine or iodine and Q, R$^1$ and R$^2$ have the above-mentioned meaning, optionally in the presence of a diluent and in the presence of a base.

3. Pesticidal composition comprising at least one substituted nitrogen heterocycles of the formula (I)

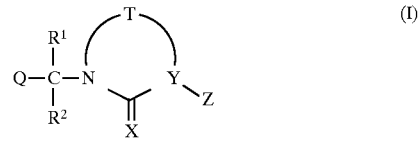

in which the group

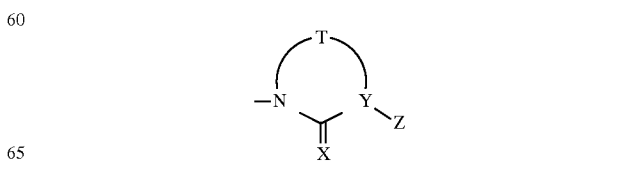

represents one of the following meanings:

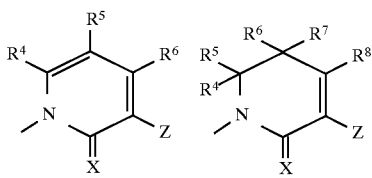

where
R$^1$ represents hydrogen, methyl or ethyl,
R$^2$ represents hydrogen,
X represents oxygen, sulphur or NR$^3$,
Z represents a cyano or nitro group,
Q assumes one of the following meanings

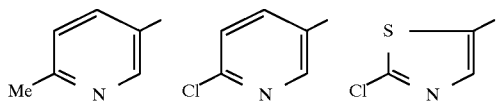

R$^3$ represents hydrogen or methyl, and
R$^4$, R$^5$, R$^6$, R$^7$ and R$^8$ independently of one another represent hydrogen, fluorine, chlorine, bromine, C$_{1-2}$-alkyl, C$_{1-2}$-alkoxy and phenyl which is optionally mono- or polysubstituted by fluorine, chlorine, bromine, C$_{1-2}$-alkyl, trifluoromethyl, C$_{1-2}$-alkoxy or trifluoromethoxy.

4. Method of combating pests comprising allowing substituted nitrogen heterocycles of the formula (I) according to claim 3, to act on pests and/or their environment.

5. Process for the preparation of pesticides comprising mixing substituted nitrogen heterocycles of the formula (I) according to claim 3, with extenders and/or surface active agents.

6. Substituted nitrogen heterocycles according to claim 1, wherein
X represents sulphur or a radical NR$^3$.

7. Substituted nitrogen heterocycles according to claim 1 wherein
X represents oxygen or sulphur.

8. Process for the preparation of substituted nitrogen heterocycles according to claim 2, wherein
X represents oxygen or sulphur.

9. Pesticidal composition according to claim 3, wherein
X represents oxygen or sulphur.

* * * * *